(12) United States Patent
Harding

(10) Patent No.: US 7,717,882 B2
(45) Date of Patent: May 18, 2010

(54) MEDICAL ACCESS DEVICE

(75) Inventor: Weston F. Harding, Lehi, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 829 days.

(21) Appl. No.: 11/281,551

(22) Filed: Nov. 17, 2005

(65) Prior Publication Data

US 2007/0112314 A1 May 17, 2007

(51) Int. Cl.
*A61M 5/00* (2006.01)
(52) U.S. Cl. ...................................... 604/246
(58) Field of Classification Search .............. 604/246, 604/247
See application file for complete search history.

(56) References Cited

U.S. PATENT DOCUMENTS

| | | | | |
|---|---|---|---|---|
| 4,895,346 A * | 1/1990 | Steigerwald | ............. | 251/149.1 |
| 5,242,393 A * | 9/1993 | Brimhall et al. | ................ | 604/86 |
| 5,300,034 A * | 4/1994 | Behnke et al. | ......... | 604/167.02 |
| 5,643,227 A * | 7/1997 | Stevens | ....................... | 604/264 |
| 5,685,866 A * | 11/1997 | Lopez | ......................... | 604/249 |
| 5,807,323 A * | 9/1998 | Kriesel et al. | .................. | 604/89 |
| 5,814,024 A * | 9/1998 | Thompson et al. | ........... | 604/246 |
| 5,843,044 A * | 12/1998 | Moorehead | ................. | 604/247 |
| 5,843,046 A * | 12/1998 | Motisi et al. | ................. | 604/256 |
| 5,961,497 A * | 10/1999 | Larkin | ......................... | 604/246 |
| 5,971,965 A * | 10/1999 | Mayer | ......................... | 604/249 |
| 6,029,946 A * | 2/2000 | Doyle | ....................... | 251/149.1 |
| 6,050,978 A * | 4/2000 | Orr et al. | ..................... | 604/249 |
| 6,079,449 A * | 6/2000 | Gerber | ......................... | 137/859 |
| 6,171,287 B1 * | 1/2001 | Lynn et al. | ................... | 604/256 |
| 6,651,956 B2 * | 11/2003 | Miller | ...................... | 251/149.1 |
| 6,692,478 B1 * | 2/2004 | Paradis | ....................... | 604/403 |
| 6,755,391 B2 * | 6/2004 | Newton et al. | ........... | 251/149.6 |
| 7,033,339 B1 * | 4/2006 | Lynn | .......................... | 604/256 |
| 7,220,245 B2 * | 5/2007 | Kriesel | ....................... | 604/134 |
| 2002/0193752 A1 * | 12/2002 | Lynn | .......................... | 604/249 |
| 2003/0093061 A1 * | 5/2003 | Ganem | ........................ | 604/533 |
| 2007/0112311 A1 * | 5/2007 | Harding et al. | ............. | 604/246 |
| 2007/0112332 A1 * | 5/2007 | Harding et al. | ............. | 604/533 |
| 2008/0108956 A1 * | 5/2008 | Lynn et al. | ................... | 604/256 |

* cited by examiner

*Primary Examiner*—Nicolas D. Lucchesi
*Assistant Examiner*—Aarti B Berdichevsky
(74) *Attorney, Agent, or Firm*—Kinney & Lange, P.A.

(57) ABSTRACT

A medical access device provides needleless access to patient fluid lines such as intravascular catheters. A preformed crimp ring is attached around a septum and the top end of the housing of the medical access device. The crimp ring is configured to hold the septum in place. The septum provides access for a tubular portion of a medical device such as a male luer taper of a syringe. The crimp ring is then attached by mechanical attachment and/or chemical adhesion to the housing to minimize axial and rotational movement between the septum and the housing.

17 Claims, 9 Drawing Sheets

MEDICAL ACCESS DEVICE

BACKGROUND OF THE INVENTION

The present invention relates to a connector for accessing patient fluid lines. In particular, the present invention is an access connector that may be opened by a tubular portion of a medical device, such as a male luer taper of a syringe.

In the course of treating patients, clinicians are continually transferring patient fluids between various containers and intravascular (IV) lines or through IV catheters. Transfer of these fluids is preferably through a closed system to prevent microbes from entering the system and causing infections in the patients.

Many of these closed systems have relied on the use of a needle to penetrate a rubber or silicone septum to gain access to the fluid lines. The clinician may then inject fluid into or withdraw fluid from the patient via a needle and syringe. The septum then reseals after the needle is withdrawn, which prevents backflow of the fluids and closes the system once again.

Because of the concern over accidental puncture with needles contaminated with a patient's blood or other fluids, needleless mechanisms have been developed to access patient fluid lines. One such mechanism utilizes a silicone septum that has a slit in it wide enough to allow a standard male luer taper to access the fluids. In this type of mechanism, the silicone septum is encompassed by a thermoplastic housing. With current connectors, the septum is bonded to the housing with adhesive.

Bonding between the septum and housing prevents the septum from rotating within the housing while a male luer-lock taper is locked and unlocked from the connector. In addition, as a male luer taper is drawn out of the septum, the taper tends to stick to the septum and stretches the septum out of the housing. If the septum is not bonded to the housing, the septum will pull out, or, as the taper slips off the septum, the septum snaps back into the housing causing fluids to spatter.

BRIEF SUMMARY OF THE INVENTION

The present invention is an access connector for accessing patient fluid lines. The access connector includes a housing, a crimp ring, and a septum. The crimp ring is formed prior to being mechanically attached around the septum, which has been inserted into a channel within the housing. The septum provides a tubular portion of a medical device resealable access to the fluid line. The present invention minimizes axial and rotational movement between the housing and the septum to allow optimum performance by the connector.

DETAILED DESCRIPTION

Figure 1A:
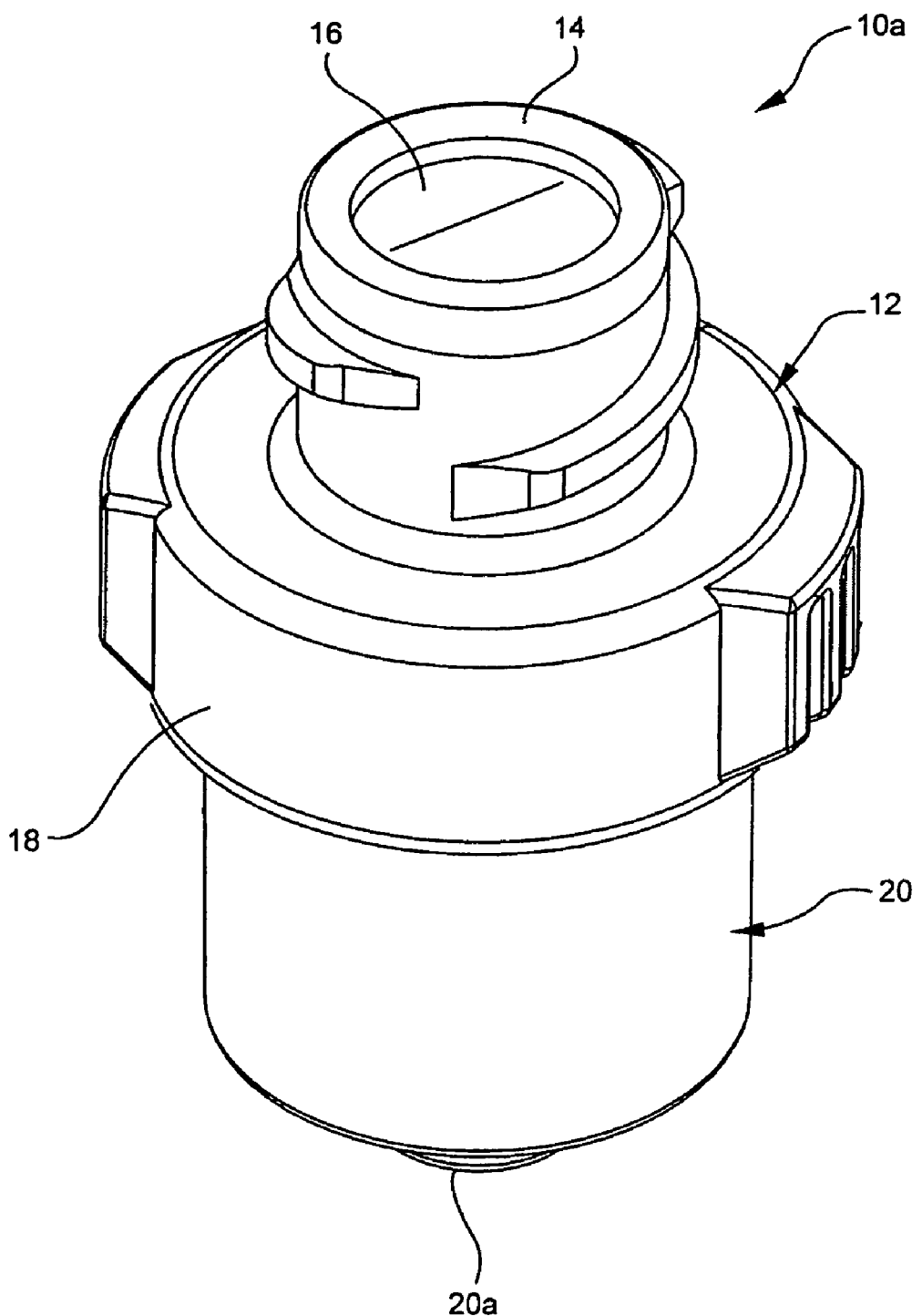
FIG. 1A is a perspective view of a first representative embodiment of an access connector.
Figure 1B:
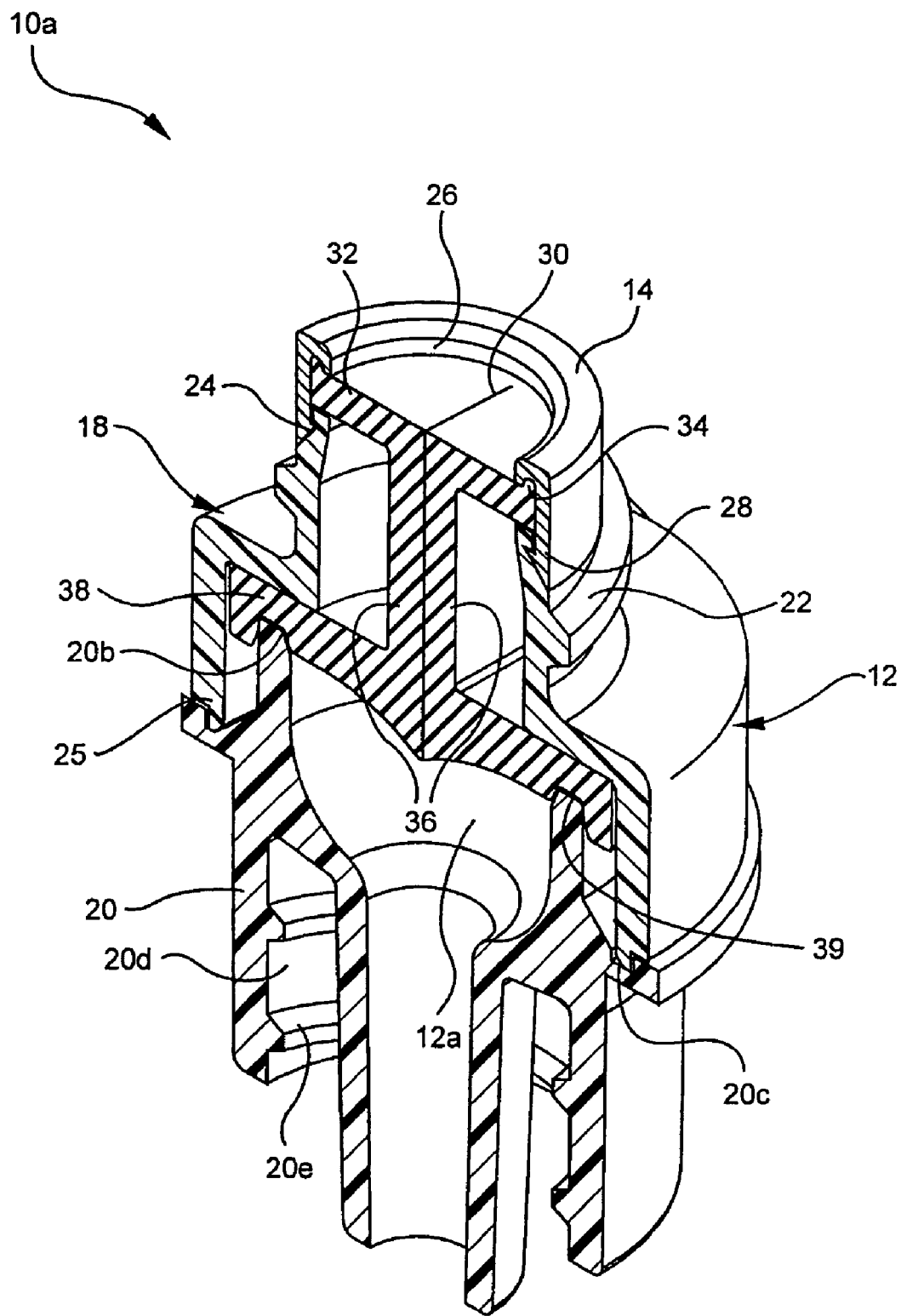
FIG. 1B is a cross-sectional view of the first access connector.
Figure 1C:
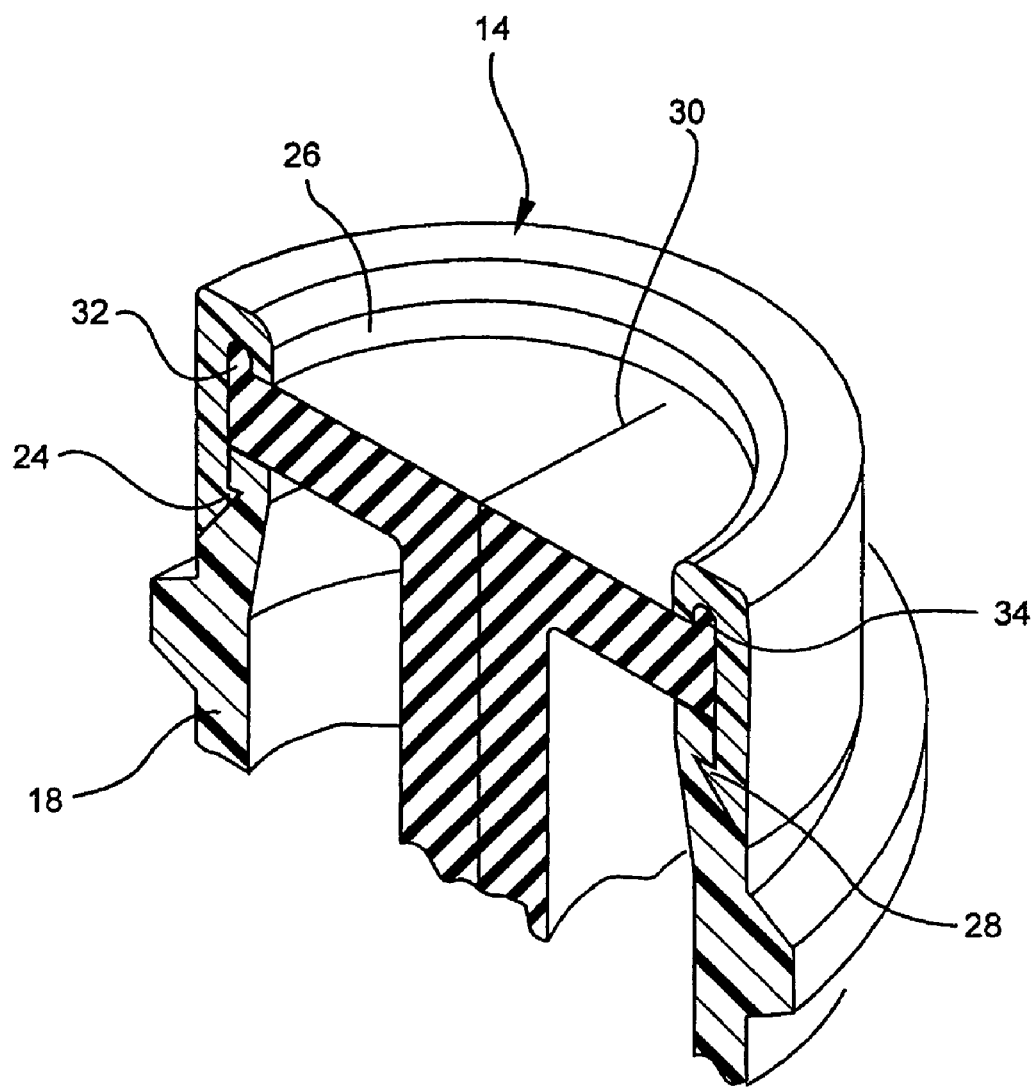
FIG. 1C is a cross-sectional view of the septum, crimp ring and housing of the first access connector.

FIGS. 1A-1C show components of a representative embodiment of access connector 10a. FIG. 1A shows access connector 10a with housing 12, crimp ring 14 and septum 16. Housing 12 also includes body 18 and base 20 with fluid line port 20a.

Housing 12 is typically made of thermoplastic material such as polycarbonate, polyester and blends of the two. Crimp ring 14 may be fabricated from the same material or same class of materials. Alternatively, crimp ring 14 may be fabricated from metal such as stainless steel or aluminum. Septum 16 is typically made from silicone or polyisoprene. Housing 12, crimp ring 14 and septum 16 may be fabricated from other materials as long as septum 16 is flexible, while housing 12 and crimp ring 14 are relatively rigid.

Crimp ring 14 surrounds the top of septum 16 and is attached to the top end of body 18. Base 20 is attached to the bottom end of body 18, and port 20a extends from the bottom end of base 20.

In use, connector 10a is connected to a patient fluid line via port 20a. The patient fluid line may be any of a number of types such as IV lines, saline wells, arterial lines, hemodialysis lines, etc. When connected, the system remains closed to prevent entry of microbes that could cause infection and back flow of any fluids out of the system. The Q-Syte™ closed luer access device from Becton, Dickinson and Company is an example of a connector that may be assembled according to the present invention.

FIG. 1B shows connector 10a in more detail. In addition to the structures shown in FIG. 1A, FIG. 1B includes fluid channel 12a of housing 12; thread 22, recess 24 and bottom edge 25 of body 18; lip 26 and barb 28 of crimp ring 14; slit 30, top disk 32 with ridge 34, column 36 and bottom disk 38 with annular groove 39 of septum 16 and rim 20b, channel 20c, sleeve 20d and thread 20e of base 20.

When assembled, bottom edge 25 of body 18 engages channel 20b of base 20 and these are bonded by ultrasonic welding, solvent bonding, adhesive bonding, etc. Rim 20b of base 20 mates with annular groove 39 of septum 16 to seal channel 12a.

FIG. 1C shows the upper portion of connector 10a in more detail. Crimp ring 14, body 18 and base 20 are formed separately, typically by injection molding unless crimp ring 14 is formed of metal. In the thermal injection molding process, the thermoplastic material used for crimp ring 14, body 18 and base 20 is rigid at room temperature and melted just prior to injecting under pressure into crimp ring-shaped, body-shaped and base-shaped molds. The thermoplastic material cools and solidifies taking the shape of each mold cavity. Once cooled, crimp ring 14, body 18 and base 20 are de-molded.

Septum 16 is also typically formed by injection molding. Here, a two-component silicone is injected into a heated septum-shaped mold cavity under pressure. The two components, which are liquid at room temperature, contact the hot mold, and react and solidify taking the shape of the mold cavity. Septum 16 is de-molded while still hot and allowed to cool outside of the mold.

To assemble connector 10a, bottom disk 38 of septum 16 is collapsed and inserted downward into body 18 until bottom disk 38 opens within body 18, or top disk 32 may be collapsed and inserted upward into body 18 until top disk 32 opens over rim 25. Base 20 is then positioned as described above and bonded by processes such as ultrasonic welding, solvent bonding, adhesive bonding, etc. to body 18. These sections readily bond, because they are fabricated from the same material or same class of materials. However, base 20 may be attached at a later point in the manufacturing process.

With the outer edges of top disk 32 positioned on the top end of body 18, crimp ring 14 is placed over septum 16 such that lip 26 of crimp ring 14 engages ridge 34 of septum 16. Alternatively, crimp ring 14 may be positioned over septum 16 prior to insertion of septum 16 into body 18. Crimp ring 14 is sized so that a slight force must be exerted in order for barb 28 of crimp ring 14 to snap into recess 24 of body 18. At this point, the components of connector 10a are secured by mechanical attachment for proper operation. When crimp ring 14 and body 18 are made of the same material or same class of material, these parts can additionally be chemically bonded by solvent bonding or adhesive bonding. It is important to note that any combination of attachment and bonding may be used.

The components of housing 12 create channel 12a through connector 10a. Septum 16 acts as a resealable seal that allows fluid to pass through when septum 16 is opened by a tubular portion of a medical device. Once assembled, connector 10a is used to access a patient fluid line. A medical device having a tubular portion, such as a male luer taper of a syringe, is used to infuse or withdraw fluids from the patient fluid line via connector 10a. The male luer taper is inserted into slit 30 of septum 16 and, if the medical device has a luer lock, rotated to interlock the medical device with connector 10a via threads 22. Medical devices that utilize a luer slip can also be used with connector 10a by simply sliding the male luer taper in place. Connector 10a may be fabricated without threads 22, but then connector 10a could only be used in combination with a luer slip and not a luer lock.

Once the male luer taper is in place, a clinician is then able to either infuse the patient fluid line or draw fluids from it. Medical devices having a luer lock are rotated in the opposite direction and pulled out for withdrawal from septum 16, while medical devices having a luer slip are simply pulled out. Crimp ring 14 is typically shaped to compress septum 16 such that slit 30 is biased shut. (This is discussed below in more detail.) The system remains closed, and the risk of entry by microbes or leakage of contaminated fluids is minimized. In addition, there is no threat of accidental needle sticks.

Attaching septum 16 by crimp ring 14 minimizes axial and rotational movement of septum 16 relative to housing 12. For instance, maintaining the attachment between septum 16 and crimp ring 14 minimizes snapback, which was previously described.

Crimp ring 14 is typically shaped such that it exerts a compressive force on septum 16 to bias slit 30 closed. In one embodiment, top disk 32 of septum 16 takes on an elliptical shape through the molding process. Slit 30 is positioned such that its longitudinal axis is perpendicular to the longitudinal axis of top disk 32. Crimp ring 14 is molded such that it takes on a substantially circular shape. When crimp ring 14 is then attached around top disk 32, it compresses top disk 32 along its longitudinal axis to bias slit 30 closed.

In a second embodiment, crimp ring 14 is molded or deformed after being molded to take on an elliptical shape and positioned relative to slit 30 such that the longitudinal axis of slit 30 is aligned with the longitudinal, uncompressed axis of crimp ring 14.

Deforming crimp ring 14 is relatively easy, because its small size makes it quite malleable. A slight force applied on each side of crimp ring 14 is enough to deform it into the elliptical shape. Body 18, which is much more rigid than crimp ring 14, will maintain crimp ring 14 in the elliptical configuration. When formed of metal, crimp ring 14 readily holds the elliptical shape.

The present invention improves the manufacture of connector 10a by eliminating the use of primer and adhesive to bond housing 12 and septum 26, which is labor intensive and requires very tight process controls. Thus, restrictions on scaling up to high volume production are reduced. In addition, the attachments are stronger and more consistent than the adhesive bonds. Variations in the configuration of the top disk and crimp ring may provide additional advantages. Examples are described below.

Figure 2A:
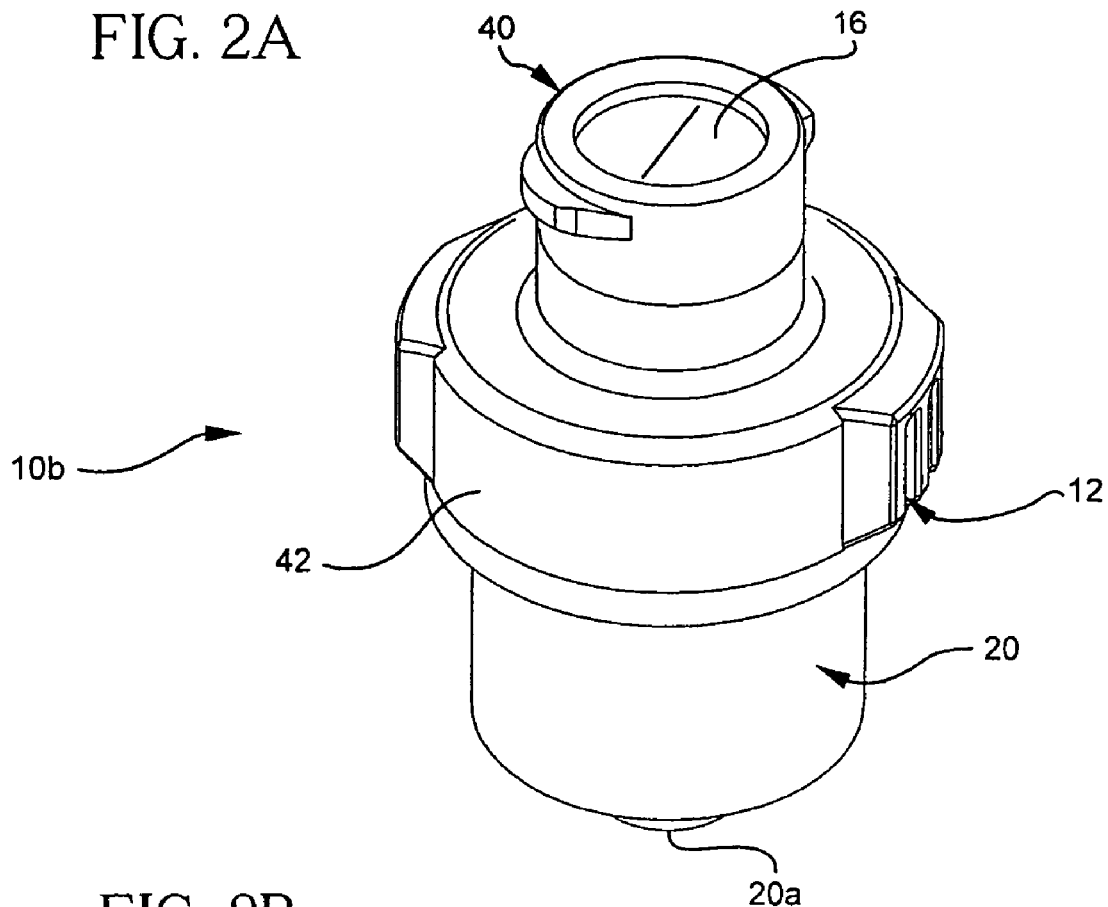
FIG. 2A is a perspective view of a second representative embodiment of an access connector.

FIG. 2A is a representative embodiment of connector 10b. Connector 10b includes housing 12, crimp ring 40 and septum 16. Housing 12 also includes body 42 and base 20 with patient fluid line port 20a.

Figure 2B:
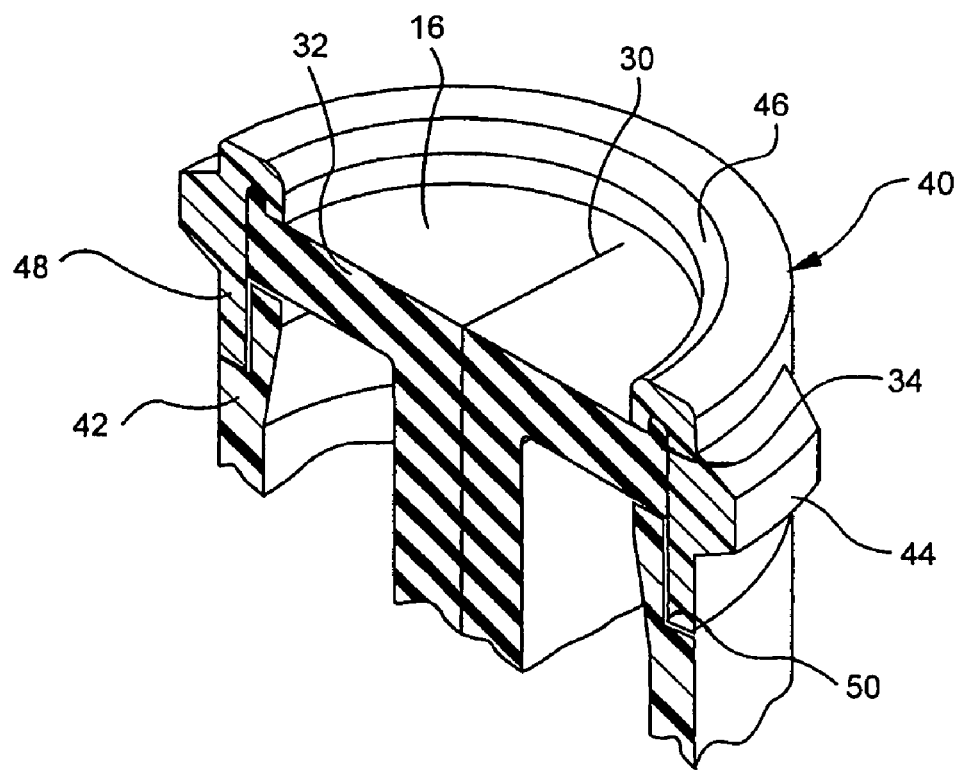
FIG. 2B is a cross-sectional view of the septum, crimp ring and housing of the second access connector.

FIG. 2B shows the upper portion of connector 10b in more detail. In addition to the structures shown in FIG. 2A, FIG. 2B also shows slit 30 and top disk 32 with ridge 34 of septum 16; lugs 44, lip 46 and sleeve 48 of crimp ring 40 and shoulder 50 of body 42.

Connector 10b is assembled as described for connector 10a, except that, unlike crimp ring 14, crimp ring 40 has no means to mechanically attach to body 42. In this embodiment, sleeve 48 is positioned on shoulder 50 of body 42. Crimp ring 40 and body 42 are then bonded by ultrasonic welding, solvent bonding, adhesive bonding, etc.

An additional difference between connectors 10a and 10b is that connector 10b uses lugs 44 instead of a thread. Lugs 44 are flange structures that are the means for interlocking with a luer lock. Lugs 44 are smaller and fabricated on crimp ring 40 instead of on body 42.

Figure 3A:
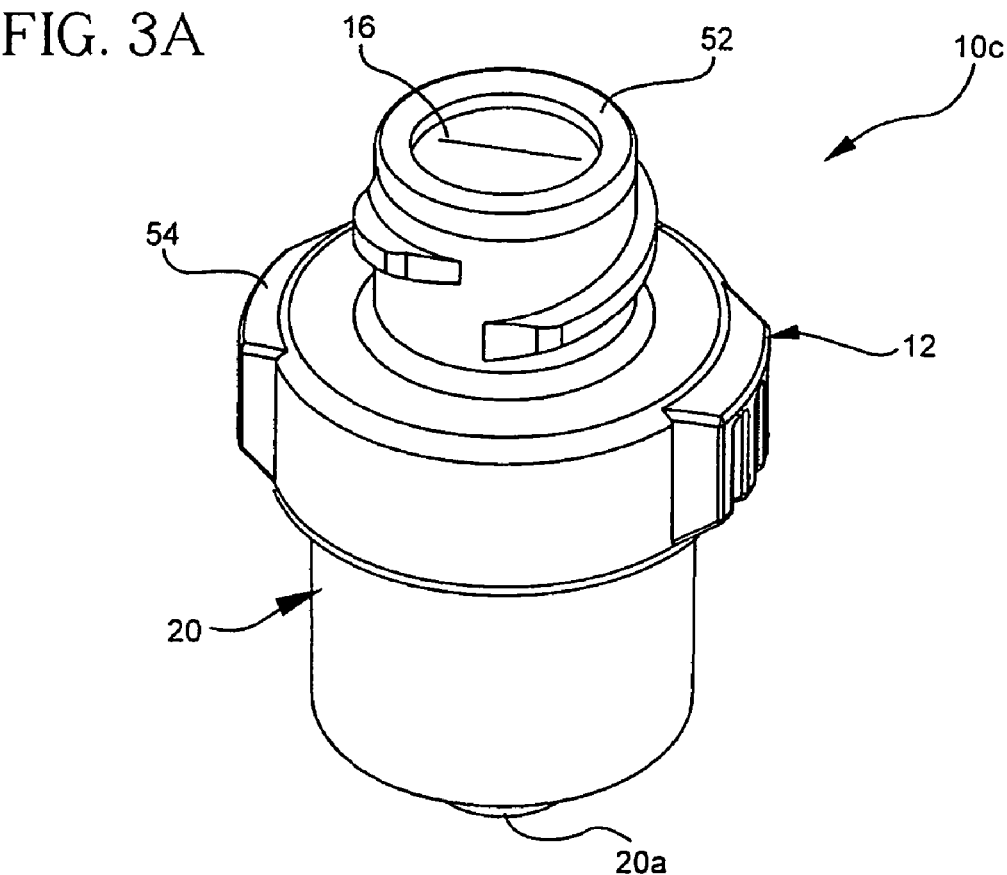
FIG. 3A is a perspective view of a third representative embodiment of an access connector.

FIG. 3A is a representative embodiment of connector 10c. Connector 10c includes housing 12, crimp ring 52 and septum 16. Housing 12 also includes body 54 and base 20 with patient fluid line port 20a.

Figure 3B:
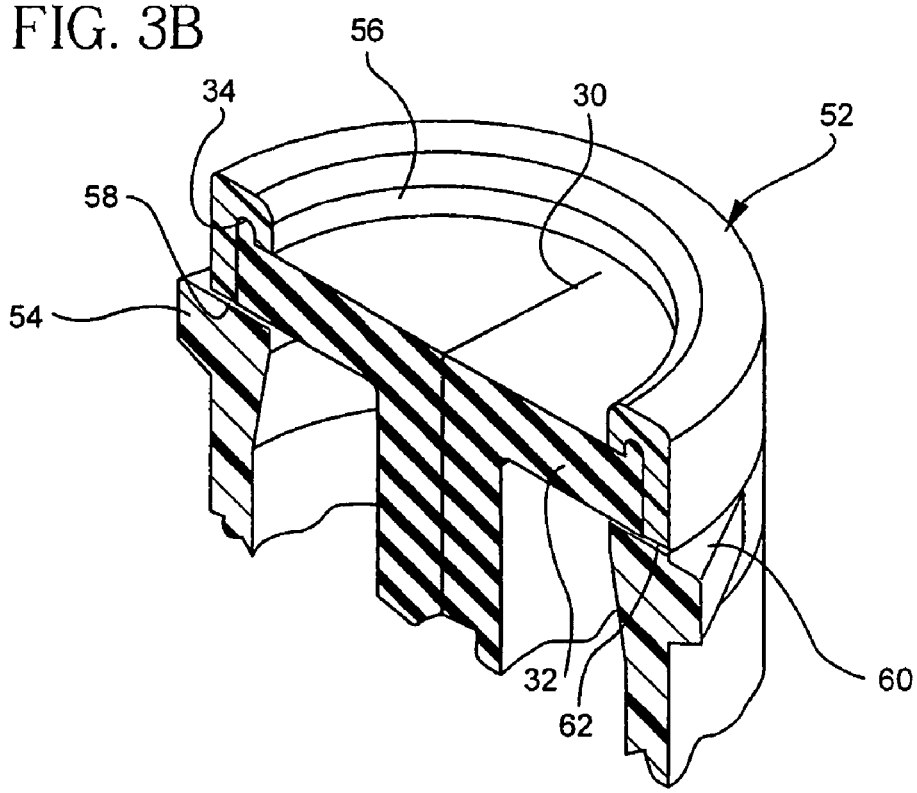
FIG. 3B is a cross-sectional view of the septum, crimp ring and housing of the third access connector.

FIG. 3B shows the upper portion of connector 10c in more detail. In addition to the structures shown in FIG. 3A, FIG. 3B also shows slit 30 and top disk 32 with ridge 34 of septum 16; lip 56 and bottom edge 58 of crimp ring 52 and thread 60 and rim 62 of body 54.

Connector 10c is similar to connector 10b except that crimp ring 52 does not have a sleeve. Instead, bottom edge 58 of crimp ring 52 is seated on rim 62 of body 54. Because there is no means for mechanical attachment, crimp ring 52 and body 54 are bonded by ultrasonic welding, solvent bonding, adhesive bonding, etc.

Figure 4A:
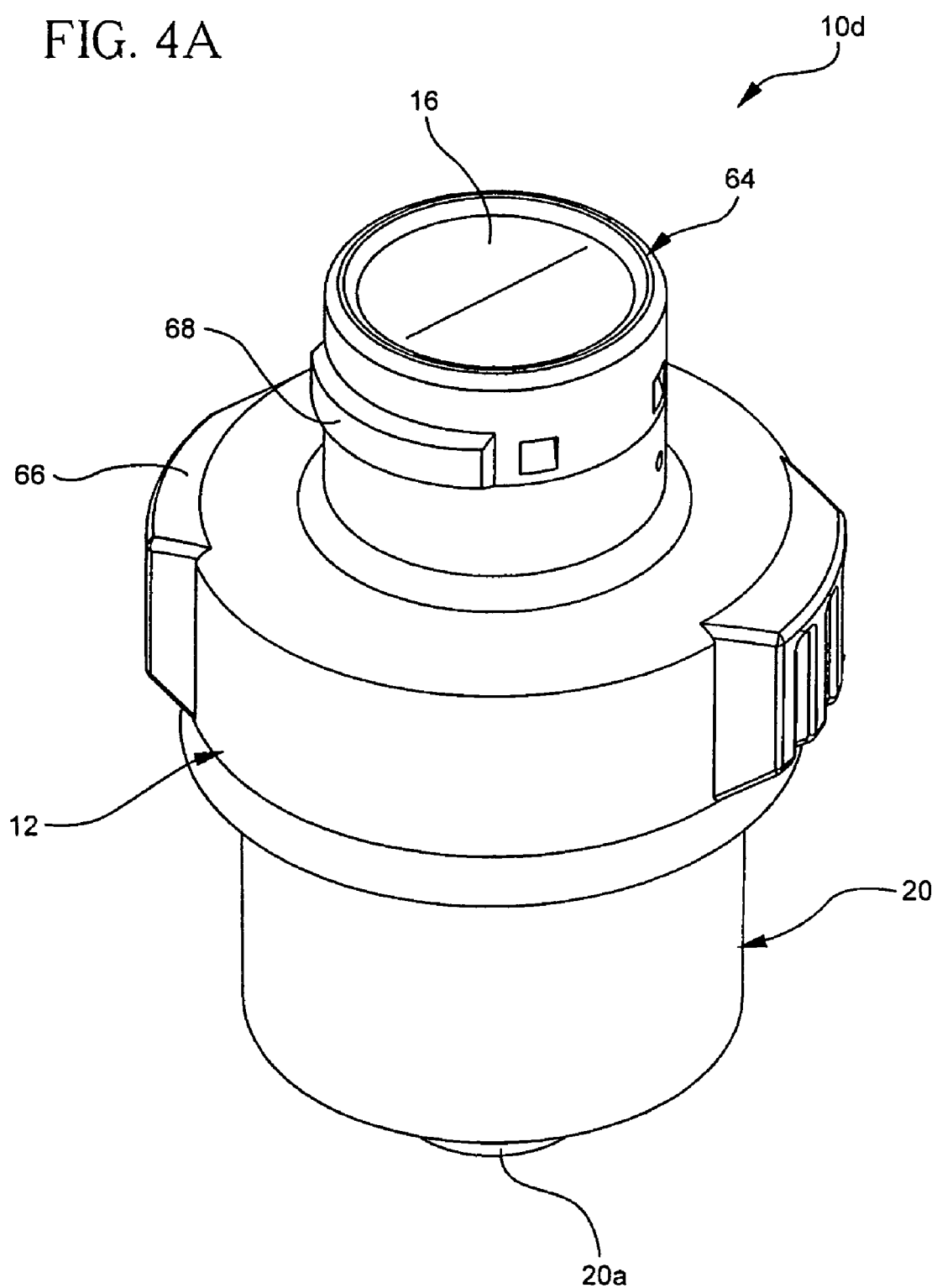
FIG. 4A is a perspective view of a fourth representative embodiment of an access connector.

FIG. 4A is a representative embodiment of connector 10d. Connector 10d includes housing 12, crimp ring 64 and septum 16. Housing 12 also includes body 66 with lugs 68 and base 20 with port 20a.

Figure 4B:
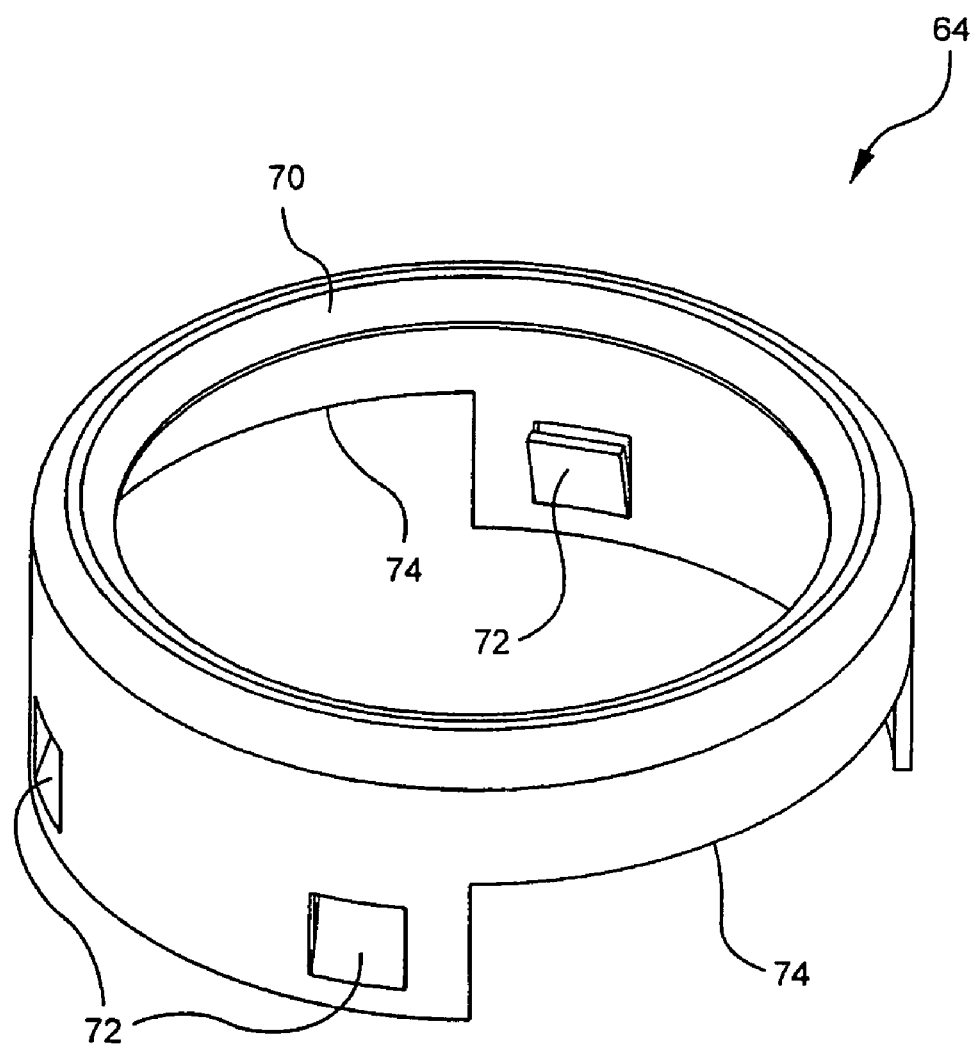
FIG. 4B is a perspective view of the crimp ring of the fourth access connector.

FIG. 4B shows crimp ring 64 in more detail. Crimp ring 64 includes lip 70, barbs 72 and cut-outs 74.

In this embodiment, crimp ring 64 is fabricated from metal. Because metal is stronger, the thickness of the metal can be thinner than the thickness of the thermoplastic, and this allows for a larger septum and housing. However, in some cases, such as in imaging procedures, metal is not a desirable material in medical devices. It is also more difficult to form threads for luer locks using metal.

To assemble connector 10d, septum 16, body 66 and base 20 are assembled as described above. Crimp ring 64 is positioned over septum 16 such that lip 70 engages ridge 34 of septum 16 (See, for example, FIG. 3B), and lugs 68 are positioned within cut-outs 74. The use of lugs 68 and cut-outs 74 overcome the difficulty associated with forming threads on crimp ring 64. Crimp ring 64 is then attached to body 66 by pressing barbs 72 into body 66. Crimp ring 64 cannot be removed once barbs 72 have penetrated the surface of body 66. Alternatively, barbs 72 may engage recesses formed within body 66. In other embodiments, an adhesive may be used in addition to or instead of barbs 72 for attaching crimp ring 64 to body 66.

Axial movement between septum 16 and crimp ring 64 is minimized as noted in previous examples. Barbs 72 and the combination of lugs 68 within cut-outs 74 also prevent rotational movement between the parts, so that connector 10d performs optimally.

Crimp ring 64 may alternatively be molded thermoplastic. However, instead of barbs 72, barbs that are similarly shaped to that shown in FIG. 1B would be required. In addition, body 66 would have recesses for engagement with the barbs, because thermoplastic barbs would not penetrate into body 66, which is also fabricated from thermoplastic. Alternatively, as with other thermoplastic crimp rings, solvent bonding and ultrasonic welding as well as adhesive bonding could be used to attach crimp ring 64 and body 66.

The configurations of the crimp rings presented above are only examples. Other configurations may also be used that will impart the advantages of the invention.

Figure 5:
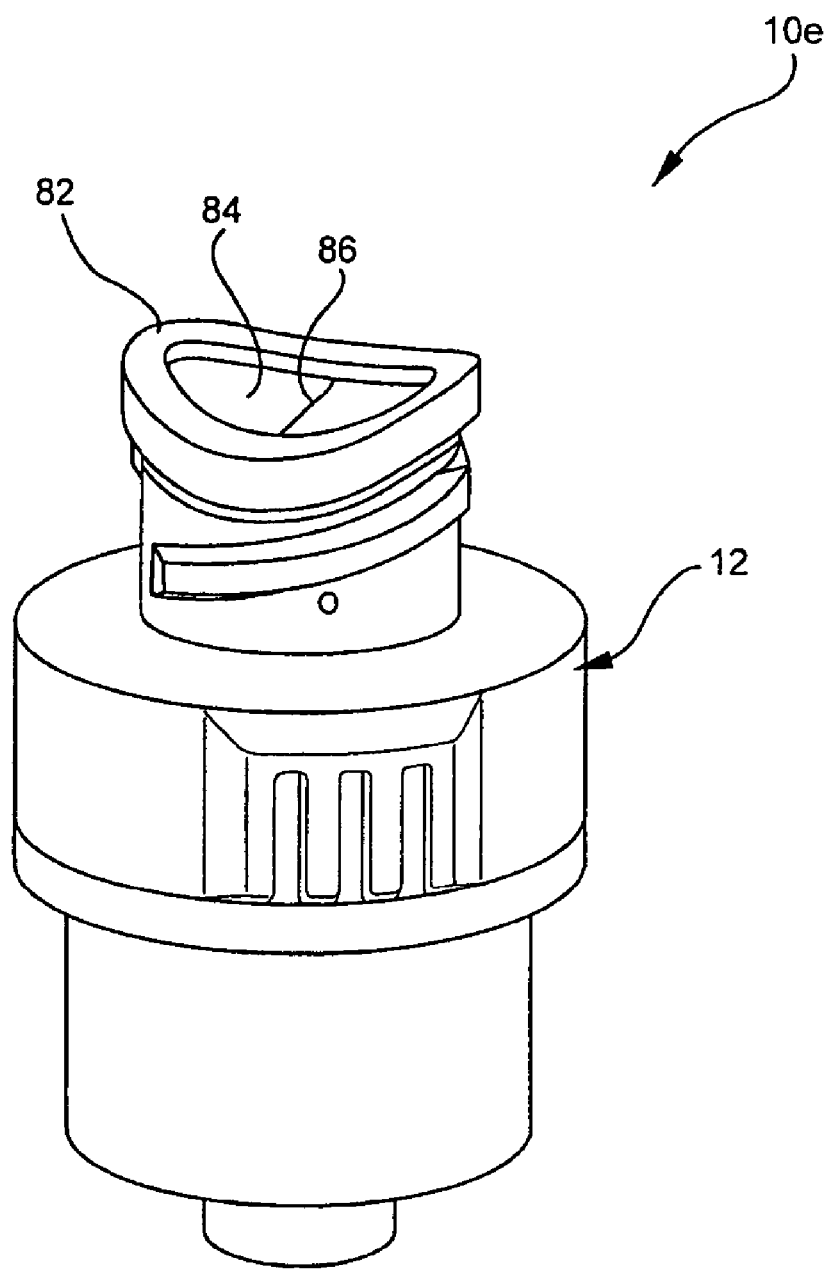
FIG. 5 is a perspective view of a fifth representative embodiment of an access connector.

Another variation is shown in FIG. 5, which is a representative embodiment of connector 10e. Connector 10e includes housing 12, crimp ring 82 and septum 84 with slit 86. Here, crimp ring 82 and septum 84 are similar to crimp ring 52 and septum 16 of connector 10c (FIGS. 3A-3B) except that crimp ring 82 and septum 84 have a saddle configuration at the top of device 10e. The saddle provides additional bias to compress slit 86 and may be combined with any configuration of connector 10 to give the advantage of biasing slit 86 closed in order to maintain a closed system.

Figure 6:
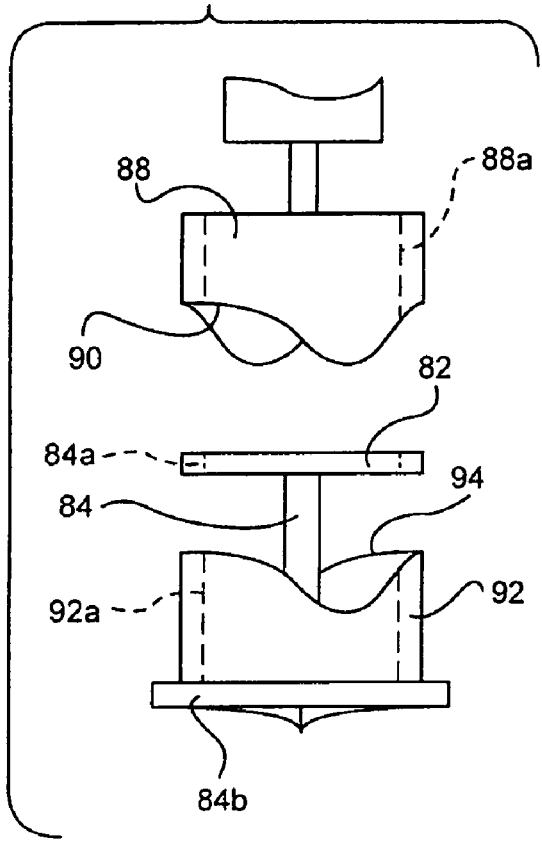
FIGS. 6 and 7 are side views showing a method of deforming a crimp ring.

FIG. 6 shows a method of forming the saddle shape of crimp ring 82 and septum 84 of connector 10e by deforming or shaping crimp ring 82. FIG. 6 shows crimp ring 82, septum 84, mandrel 88 with inner wall 88a and rim 90 and forming base 92 with inner wall 92a and rim 94. Septum 84 includes top disk 84a and bottom disk 84b.

Mandrel 88 is saddle-shaped along rim 90, heated and coated to have a non-stick surface. Forming base 92 is saddle-shaped along rim 94 in a mating fashion with rim 90 and may or may not be heated and/or coated. Both mandrel 88 and forming base 92 are cylindrical as indicated by inner walls 88a and 92a, respectively, and are sized such that rim 90 and rim 94 only contact crimp ring 82.

Figure 7:
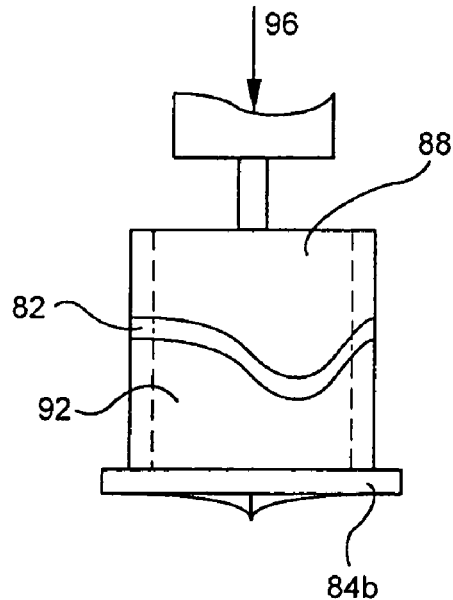

In operation, crimp ring 82 is placed over top disk 84a of septum 84 and inserted into forming base 80 such that top disk 84a is over rim 94 and bottom disk 84b is underneath forming base 92. As shown in FIG. 7, when a force is applied to mandrel 88 as indicated by arrow 96, rim 90 is pressed against crimp ring 82, which is in turn pressed against rim 94 of forming base 92. The heat and pressure causes the thermoplastic material of crimp ring 82 to form the saddle shape of mandrel 88 and forming base 92.

Depending on the type of thermoplastic material used to fabricate crimp ring 82, crimp ring 82 and septum 84 may be retained between mandrel 88 and forming base 92 until the part cools in order to maintain the saddle shape. Septum 84 is fabricated from elastomeric silicone, which has a resilient quality, and therefore will have a tendency to return to its original shape. If crimp ring 82 is not stiff enough when hot to hold the saddle shape, then crimp ring 82 and septum 84 will need to remain between mandrel 88 and forming base 92 until cool. On the other hand, if crimp ring 82 is stiff enough when hot it can be removed and allowed to cool without the support of mandrel 88 and forming base 92.

Figure 8:
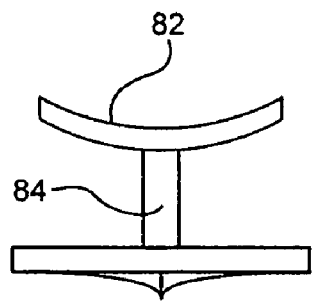
FIG. 8 is a side view of a deformed crimp ring and septum.

FIG. 8 shows crimp ring 82 and septum 84 after deformation by the above process. The parts are subsequently inserted into and attached to housing 12 to form connector 10e.

Mechanically attaching a crimp ring around the septum of access connectors according to the present invention provides several advantages. The attachment between the parts is strong and consistent. In addition, the process is a method that can be scaled up for high volume production.

Although the present invention has been described with reference to preferred embodiments, workers skilled in the art will recognize that changes may be made in form and detail without departing from the spirit and scope of the invention.

The invention claimed is:

1. An access connector comprising:
   a housing having a body and a base, the base including an annular channel for receiving a bottom edge of the body and a rim extending upwardly from the annular channel into the body;
   a septum having a top disk, a bottom disk with an annular groove in a bottom surface, a column extending between the top disk and the bottom disk, and a resealable slit extending through the top disk, column, and bottom disk to allow for insertion of a tubular portion of a medical device; and
   a crimp ring mechanically attached to the top disk of the septum and attached to a top end of the body of the housing by chemical bonding, mechanical attachment, or a combination thereof, such that the crimp ring minimizes axial and rotational movement between the septum and the housing,
   wherein the septum is positioned within the housing such that the annular groove in the bottom surface of the bottom disk is engaged by the rim of the base, an outer portion of the bottom disk is held between the body and the rim, and an outer portion of the top disk is held between the crimp ring and the top end of the body,
   wherein the slit extending through the top disk is biased closed by the crimp ring and the slit extending through the bottom disk is biased closed by the rim, the slit being opened by insertion of a tubular medical device therethrough to allow fluid flow through the septum.

2. The access connector of claim 1 wherein the crimp ring is fabricated from one of thermoplastic and metal.

3. The access connector of claim 1 and further comprising:
   a lip on the crimp ring; and
   a ridge on the top disk of the septum engaged with the lip.

4. The access of connector of claim 1 and further comprising:
   a barb on the crimp ring; and
   a recess on the body for engaging the barb.

5. The access connector of claim 1 and further comprising:
   a barb on the crimp ring, the barb penetrating the surface of the body.

6. The access connector of claim 1 wherein the crimp ring is bonded to the body by one of ultrasonic welding, solvent bonding and adhesive bonding.

7. An access connector comprising:
a septum having a top disk, a bottom disk with an annular groove in a bottom surface, a column extending between the top disk and the bottom disk, and a resealable slit extending through the top disk, column, and bottom disk;
a crimp ring mechanically attached to the top disk of the septum, the crimp ring being formed prior to attachment to the top disk; and
a housing attached to the crimp ring by chemical bonding, mechanical attachment, or a combination thereof, such that the crimp ring minimizes axial and rotational movement between the septum and the housing and forms a resealable channel with the septum for accessing a patient fluid line with a tubular portion of a medical device, the housing including a body and a base, the base having an annular channel for receiving a bottom edge of the body and a rim extending upwardly from the annular channel into the body;
wherein the septum is positioned within the housing such that the annular groove in the bottom surface of the bottom disk is engaged by the rim of the base, an outer portion of the bottom disk is held between the body and the rim, and an outer portion of the top disk is held between the crimp ring and a top end of the body,
wherein the slit extending through the top disk is biased closed by the crimp ring and the slit extending through the bottom disk is biased closed by the rim, the slit being opened by insertion of a tubular medical device therethrough to allow fluid flow through the septum.

8. The access connector of claim 7 wherein the chemical bonding is one of ultrasonic welding, solvent bonding and adhesive bonding.

9. The access connector of claim 7 wherein the crimp ring and body are snapped together.

10. The luer access connector of claim 7 and further comprising:
at least one cut-out in the crimp ring; and
at least one lug on the housing positioned within the cut-out.

11. The access connector of claim 7, further comprising:
a lip extending around the crimp ring; and
a ridge extending around the top disk of the septum, the ridge engaged with the lip.

12. A method of making an access connector, the method comprising:
positioning a crimp ring over a top disk of a septum having a slit extending from the top disk to a bottom disk;
inserting the septum within a housing having a body to form a resealable channel including the slit within the housing;
attaching the crimp ring to a top end of the housing, such that an outer portion of the top disk of the septum is held between the crimp ring and the top end of the housing thereby biasing the slit at the top disk of the septum closed; and
attaching a base to a bottom of the housing, the base having an annular channel for receiving a bottom edge of the body and a rim extending upwardly from the annular channel into the body;
wherein an annular groove in a bottom surface of the bottom disk is engaged by the rim, and an outer portion of the bottom disk of the septum is held between the body and the rim, thereby biasing the slit at the bottom disk closed.

13. The method of claim 12 wherein the crimp ring is formed of thermoplastic or metal.

14. The method of claim 12 wherein the crimp ring and housing are attached by chemical bonding, mechanical attachment or a combination thereof.

15. The method of claim 12 wherein attaching the crimp ring to the housing further comprises:
pressing at least one barb into the housing.

16. The method of claim 12 wherein positioning the crimp ring further comprises:
engaging a lip of the crimp ring with a ridge of the septum.

17. The method of claim 12 and further comprising:
contacting the crimp ring with a mandrel and forming base to deform the crimp ring.

* * * * *